(12) United States Patent  (10) Patent No.: US 6,709,403 B1
Ratner  (45) Date of Patent: Mar. 23, 2004

(54) MANOMETER $CO_2$ DETECTOR COMBINATION

(75) Inventor: Jeffrey B. Ratner, Pinellas Park, FL (US)

(73) Assignee: Mercury Enterprises, Inc., Clearwater, FL (US)

( * ) Notice: Subject to any disclaimer, the term of this patent is extended or adjusted under 35 U.S.C. 154(b) by 0 days.

(21) Appl. No.: 10/337,493

(22) Filed: Jan. 7, 2003

(51) Int. Cl.⁷ ................................................ A61B 5/00
(52) U.S. Cl. ..................... 600/532; 600/538; 73/23.3; 422/84
(58) Field of Search .................... 600/532–3, 538; 73/23.3; 422/84; 128/204.23

(56) References Cited

U.S. PATENT DOCUMENTS

| | | | |
|---|---|---|---|
| 4,353,366 A | * 10/1982 | Bickford | ................ 128/205.12 |
| 4,462,258 A | 7/1984 | Boddy | |
| 4,676,107 A | 6/1987 | Hixenbaugh et al. | |
| 4,790,327 A | 12/1988 | Despotis | |
| 4,928,687 A | 5/1990 | Lampotang et al. | |
| 5,005,572 A | 4/1991 | Raemer et al. | |
| 5,109,838 A | 5/1992 | Elam | |
| 5,166,075 A | * 11/1992 | Fehder | ....................... 436/133 |
| 5,241,863 A | 9/1993 | Molnar | |
| 5,679,884 A | * 10/1997 | Kirk | ........................... 73/23.3 |
| 5,749,358 A | 5/1998 | Good et al. | |
| 6,058,933 A | 5/2000 | Good et al. | |
| 6,123,075 A | 9/2000 | Kirk | |
| 6,378,522 B1 | 4/2002 | Pagan | |

* cited by examiner

*Primary Examiner*—Robert L. Nasser
(74) *Attorney, Agent, or Firm*—Larson & Larson, PA; James E. Larson

(57) ABSTRACT

A top and bottom housing joined together have a patient port and ventilation port in axial alignment. The top housing contains dry indicator paper for changing color in response to the presence of $CO_2$. In addition, a shaft having a pointer on a top portion rotates in response to air in the housing to indicate pressure. A helical outer wall of the shaft engages a notch in a hollow stem attached to a membrane in the lower housing so the shaft rotates in response to air pressure on the membrane.

18 Claims, 8 Drawing Sheets

MANOMETER $CO_2$ DETECTOR COMBINATION

BACKGROUND OF THE INVENTION

This invention relates to manometer and $CO_2$ detectors used in patient ventilation systems. More particularly, it refers to a disposable apparatus combining both a manometer and calorimetric $CO_2$ detection device in a patient monitor receiving exhaled air from a patient.

Manometers for measuring air pressure in a patient ventilation system and $CO_2$ detectors for determining the presence of $CO_2$ above the $CO_2$ in ambient air coming from an intubated patient are well known. Ports have to be inserted on the patient ventilation system for both the manometer and $CO_2$ detector. This creates additional work and expenditure of time for the caregiver. It would be desirable to have a single disposable monitor connected to the patient recording both air pressure and the presence of $CO_2$ in exhaled air. No such disposable monitor exists at present.

SUMMARY OF THE INVENTION

This invention solves the problem of the prior art by providing a self-contained disposable monitor recording both air pressure and the existence of $CO_2$ in a patient's exhaled breath in the same instrument. The monitor has two housing components which when joined together have a patient port and an input port. The top housing component contains calorimetric $CO_2$ indicator paper and a shaft with a helical external configuration. A pointer in a top portion of the top housing rotates with the shaft. A clear cover contains indicia for noting air pressure in the monitor as the shaft turns. The bottom housing has a receptacle for a spring that exerts pressure on a membrane above the spring. A pair of baffles and a filter between the baffles contain bores for receipt of a hollow stem directed upwardly from the center of the membrane. The inner wall of the stem has a notch for receipt of the helical configuration on the shaft in the upper housing. As exhaled air flows into the monitor from the patient, the air pressure is indicated by the pointer which turns in response to air pressure on the membrane and the $CO_2$ indicator paper changes color in response to the $CO_2$ level in the exhaled breath coming from the patient.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION OF THE BEST MODE

Figure 1:
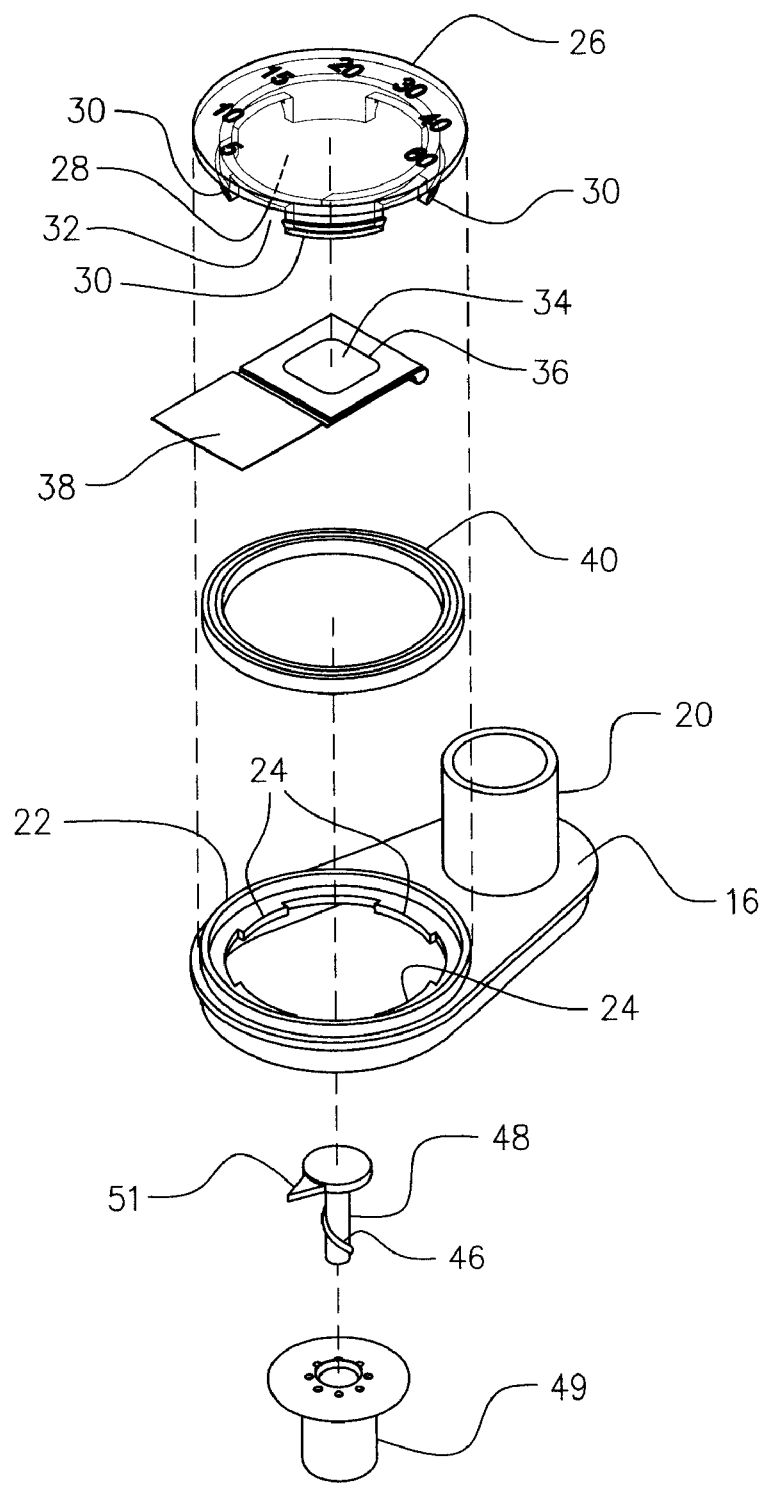
FIG. 1 is an exploded view of the top portion of the manometer $CO_2$ detector.

Throughout the following detailed description, the same reference numerals refer to the same elements in all figures.

Referring to FIGS. 1–4, the monitor 10 of this invention contains integrated elements indicating a patient's exhaled breath pressure and at the same time continued confirmation that an endotrachael tube 12 connected to port 14 of monitor 10 is properly inserted in the patient's trachea. The monitor 10 has a top housing portion 16 and a bottom housing portion 18.

Top housing portion 16 contains an inhale/exhale port 20 that can lead to a cardiopulmonary resuscitator bag or other ventilation system. In addition, top housing 16 has an annular support ring 22 containing inwardly projecting flanges 24. A clear plastic cover or disc 26 containing indicia within an outer portion has a bottom surface 28 and multiple legs 30 descending from an outer periphery of bottom surface 28. A slot 32 is formed between two legs 30.

A top surface 34 of calorimetric indicator paper 36 is adhered by adhesive to bottom surface 28 of cover 26. The calorimetric indicator paper 36 has a backing paper 38 attached to a lower surface of the indicator paper 36. A sealing ring 40 separates the cover 26 from support ring 22 as the cover 26 is snapped in place over support ring 22. When the backing paper 38 is removed so that the bottom surface of the calorimetric indicator paper is exposed to a patient's exhaled breath, the sealing ring 40 closes off opening 32 through which the backing paper 38 is pulled.

Figure 2:
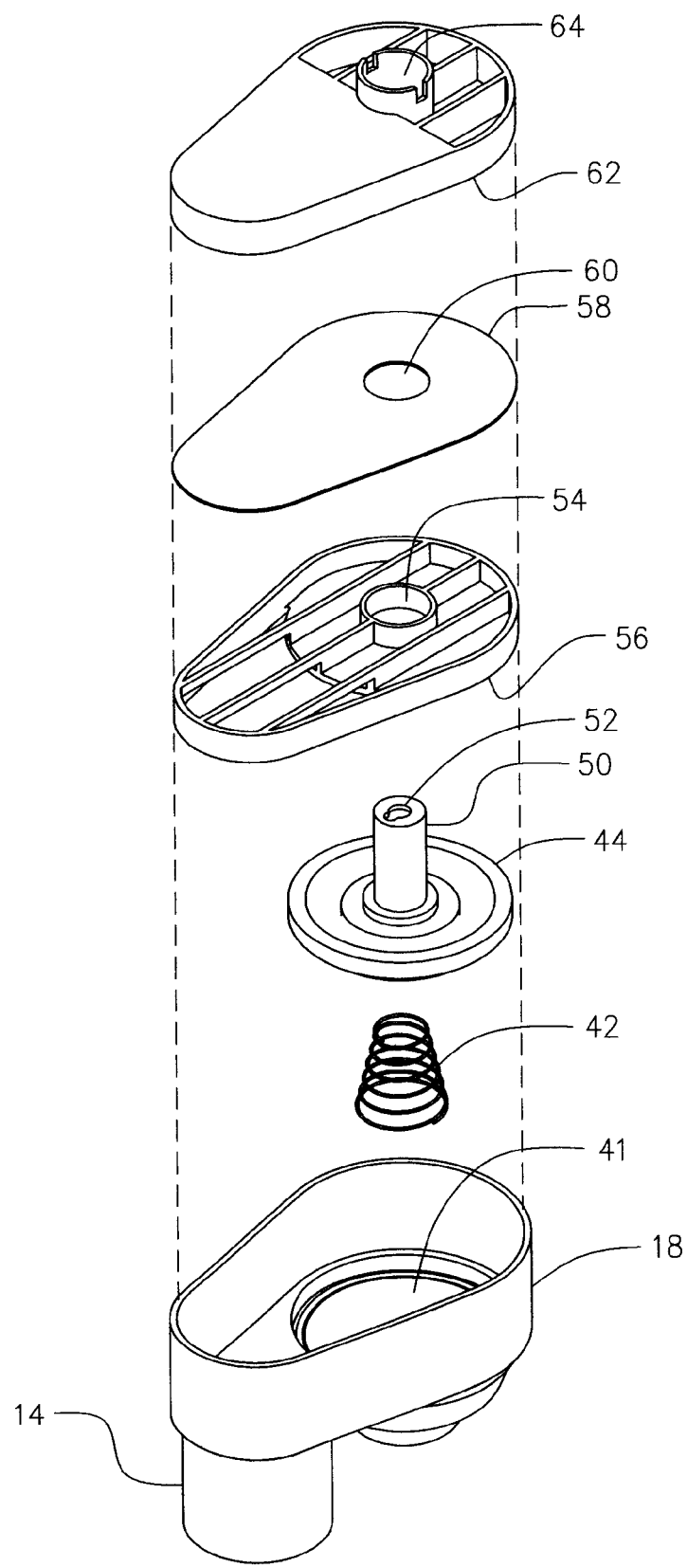
FIG. 2 is an exploded view of the bottom portion of the manometer $CO_2$ detector.
Figure 3:
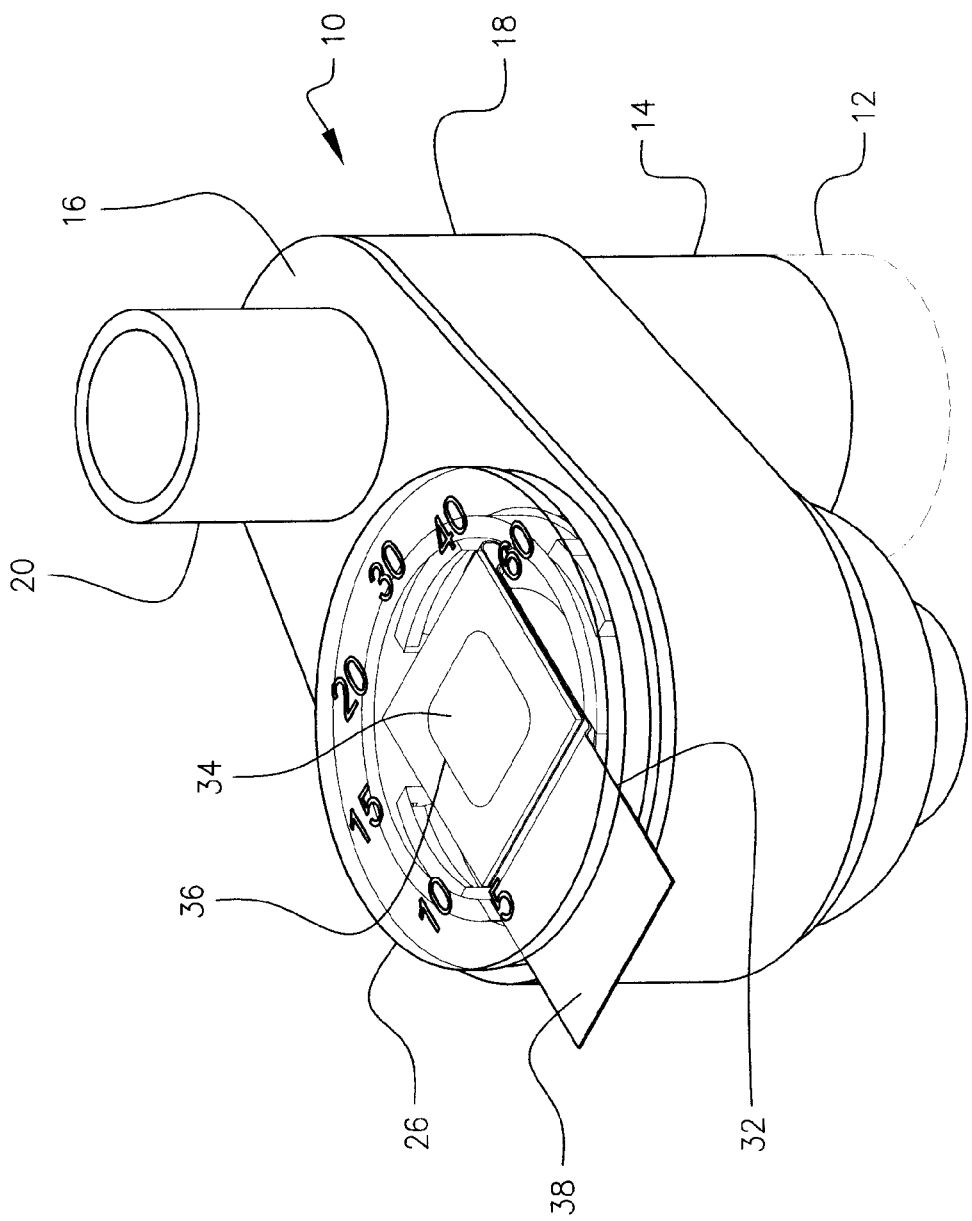
FIG. 3 is a perspective view of the manometer $CO_2$ detector with projecting backing paper.
Figure 4:
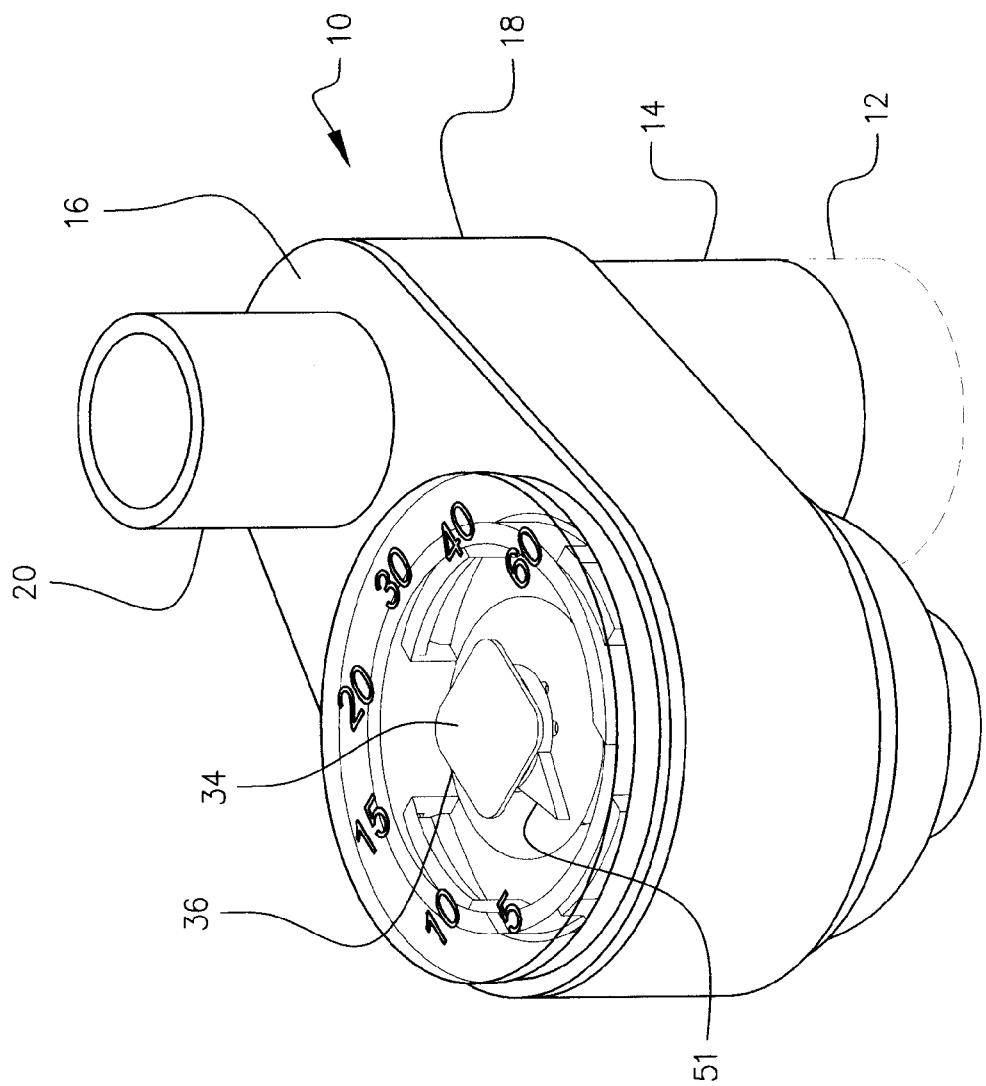
FIG. 4 is a perspective view of the manometer $CO_2$ detector of FIG. 3 after the backing paper is removed.
Figure 5:
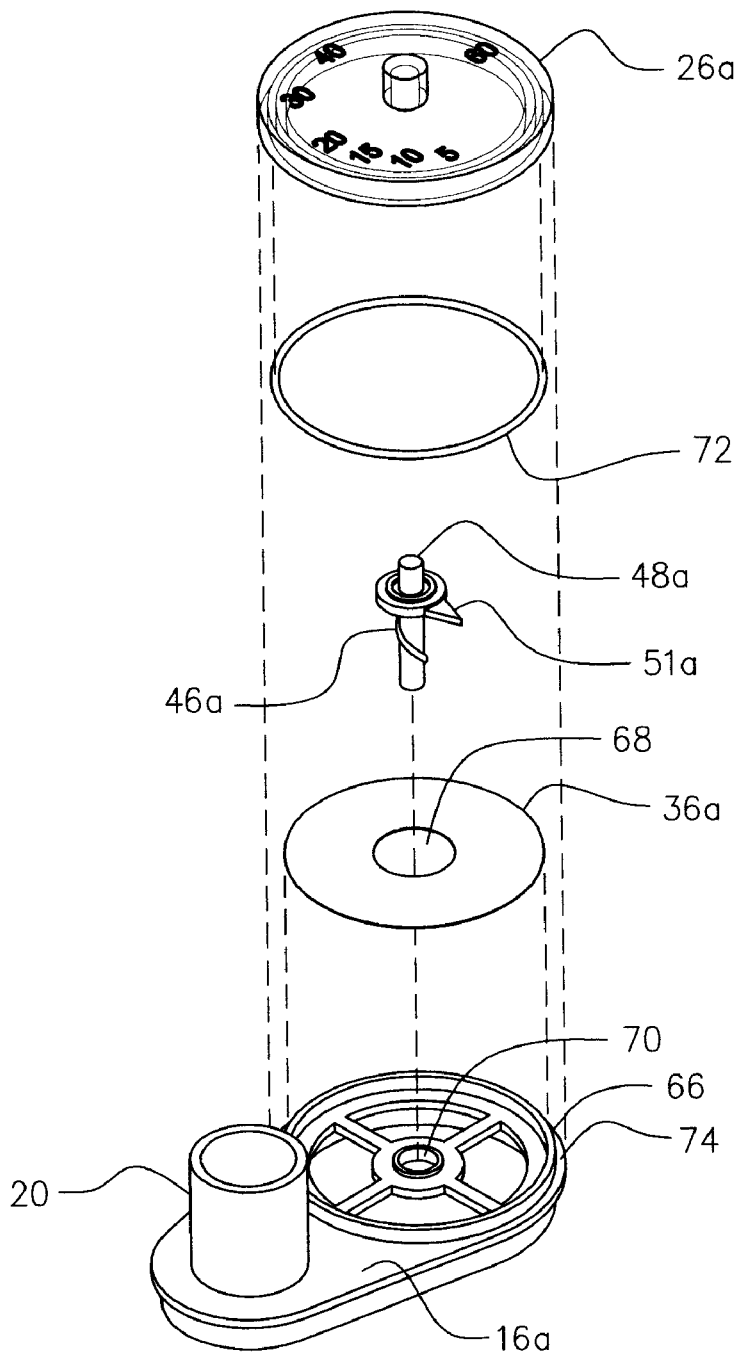
FIG. 5 is an exploded view of an alternate top portion of the manometer $CO_2$ detector.

Referring to FIG. 2, the bottom housing 18 contains the patient port 14 at one end and an internal receptacle 41 at a second distal end in which a spring 42 is positioned. A diaphragm 44 overlays the spring 42 and a hollow stem 50 extends upwardly from the diaphragm 44. The stem 50 has a notch 52 along an inner wall to receive the helix 46 around the downwardly descending shaft 48. A guide 49 for shaft 48 overlies stem 50. The shaft 48 turns a pointer 51.

Stem 50 protrudes upwardly through a hole 54 in a first baffle 56, a hole 60 in filter 58 and a hole 64 in second baffle 62. The diaphragm 44 moves in response to the exhaled breath of the patient. Movement of diaphragm 44 causes shaft 48 to turn along with pointer 51. The exhaled breath passes underneath calorimetric indicator paper 36 and causes the indicator paper to change color, confirming that the endotrachael tube remains in the correct position in the patient's trachea.

An alternate embodiment of a monitor 10a is seen in FIGS. 5–8. The difference between monitor 10 and 10a lies in the top portion of the monitor seen in FIG. 5. The top housing 16a has an annular support 66 within which a $CO_2$ calorimetric indicator impregnated paper 36a is positioned.

The indicator paper 36 and 36a is impregnated with a $CO_2$ color change composition well known in the prior art such as described in U.S. Pat. Nos. 5,005,572 and 5,965,061, incorporated herein by reference.

The indicator paper 36a has a central hole 68 axially aligned with a central hole 70 in the annular support 66. A pointer 51a turns with shaft 48a. The shaft 48a has a helix structure 46a on an outer surface. The shaft 48a protrudes downwardly within holes 68 and 70. An O-ring 72 sits on an outer edge 74 of the support 66. A clear plastic cover 26a encloses the shaft 48a and indicator paper 36a. The plastic cover 26a has indicia printed on it to facilitate indication of air pressure in the same manner as monitor 10.

Figure 6:
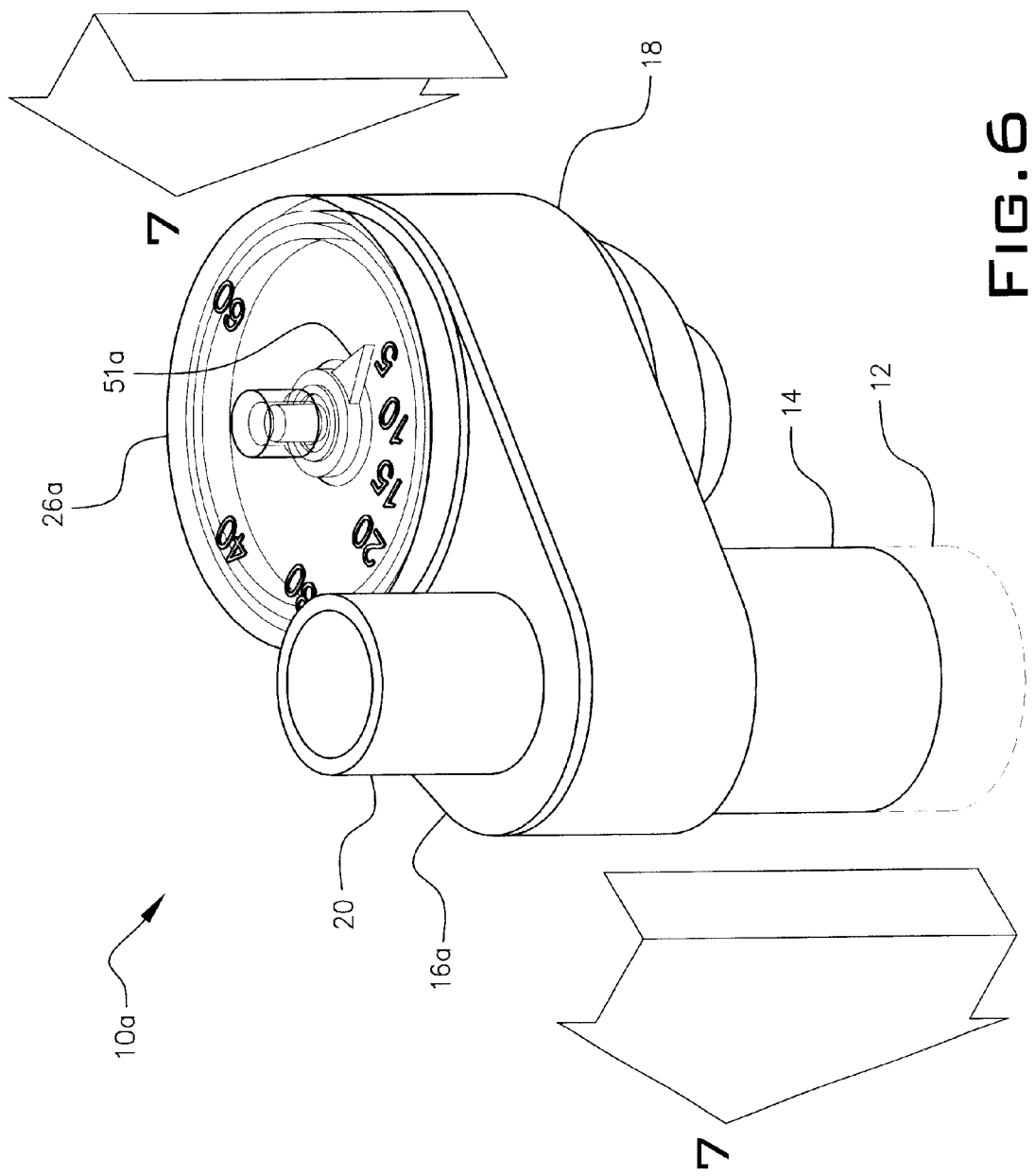
FIG. 6 is a perspective view of the alternate manometer $CO_2$ detector.

The bottom housing portion of monitor 10a is the same as seen in FIG. 2. Shaft 48a with helix 46a slides into hollow stem 50 and the helix 46a is engaged in notch 52. FIG. 6 shows monitor 10a assembled.

Figure 7:
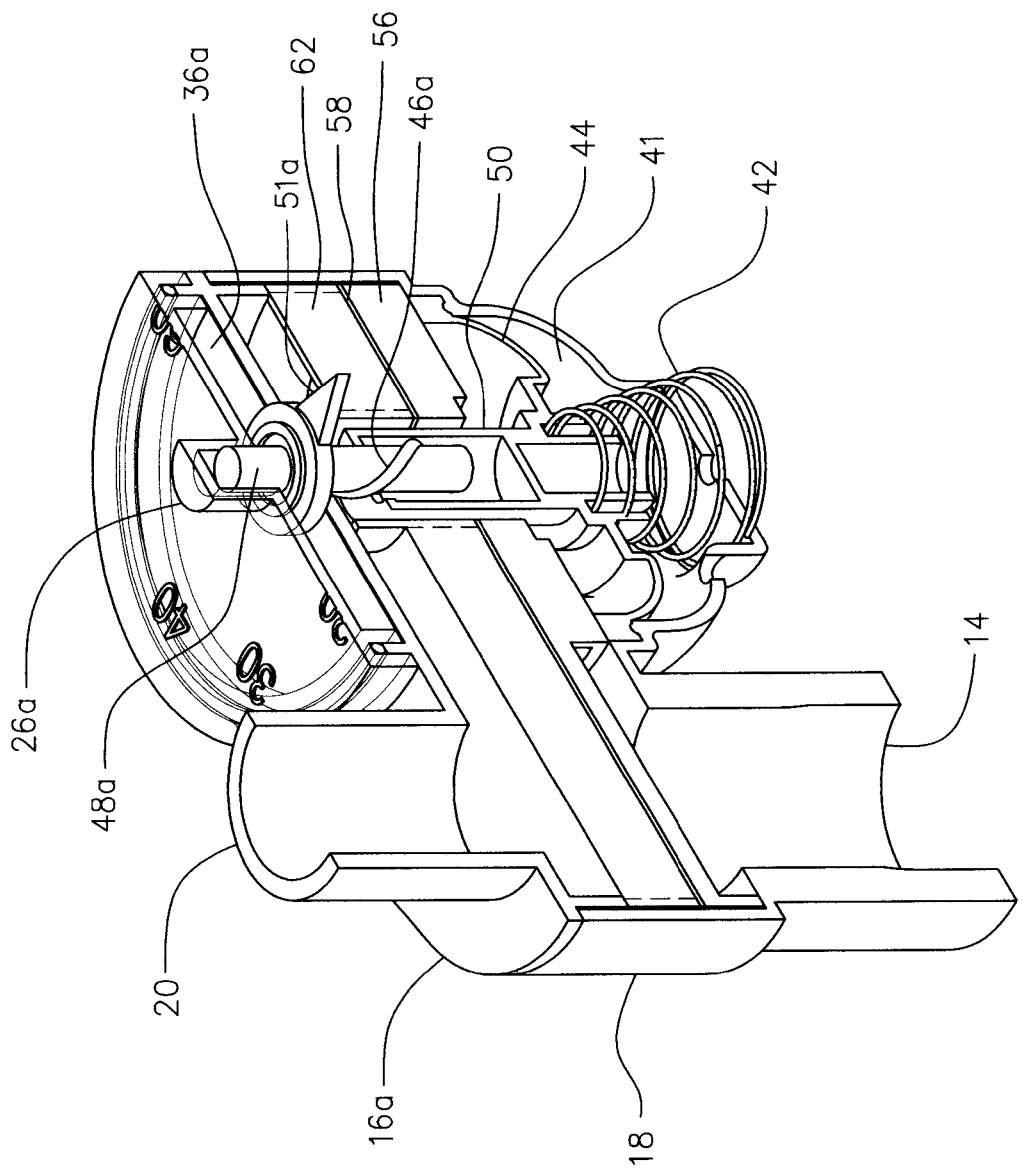
FIG. 7 is a sectional view through lines 7—7 of FIG. 6 when the manometer is not indicating a patient breath.
Figure 8:
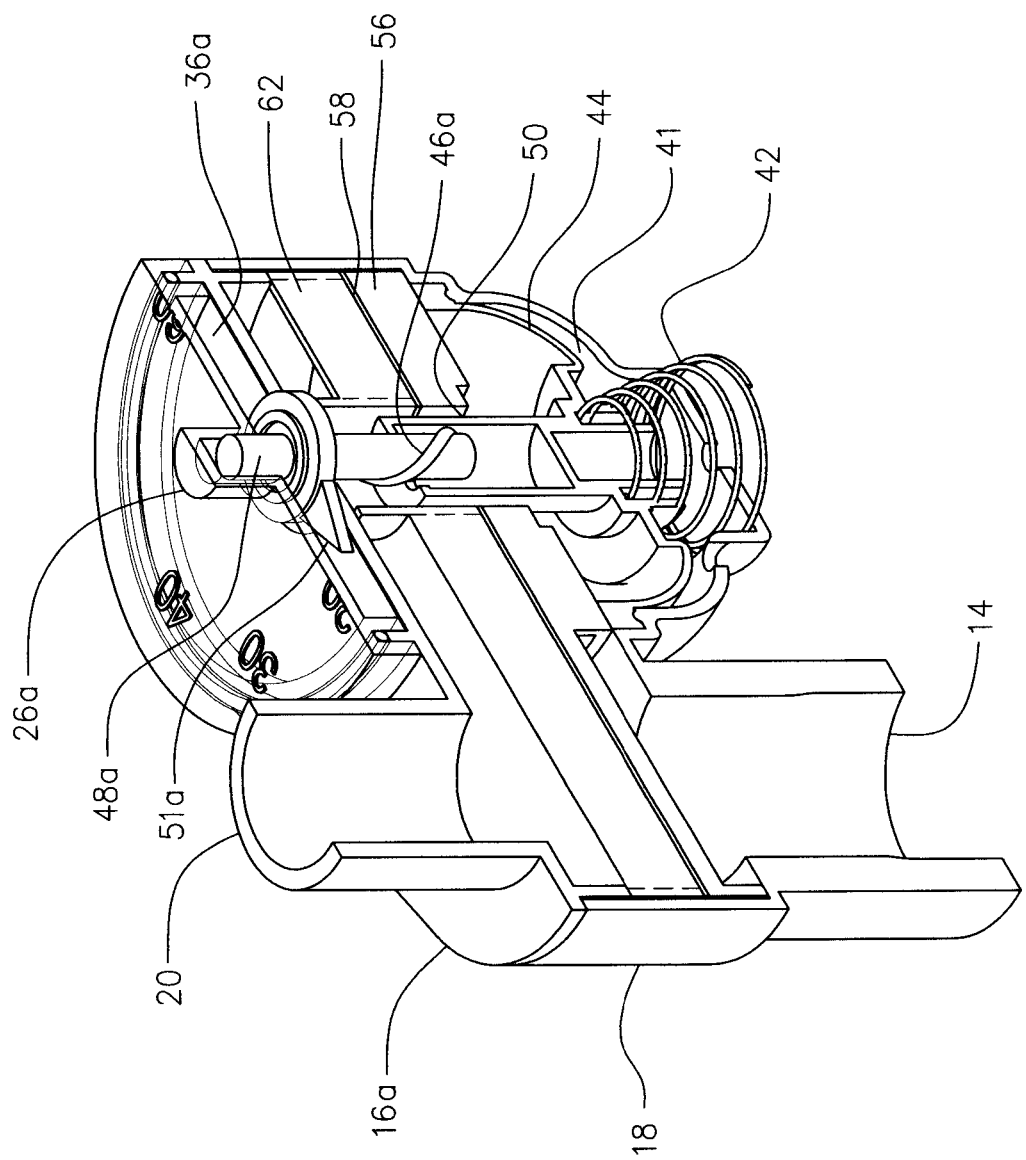
FIG. 8 is a sectional view through lines 7—7 of FIG. 6 when the manometer is indicating patient breathing.

Referring to FIGS. 7 and 8, spring 42 in FIG. 7 is not under tension since no air is passing through the manometer from the patient. In FIG. 8 air is passing through the manometer as shown by pointer 51a pointing towards a number on the indicia scale. The air pressure causes diaphragm 44 to move downwardly along with stem 50 that contains the helix structure 46a and shaft 48a connected to pointer 51a. As the patient's breath passes under $CO_2$ indicator paper 36a, a color change reveals $CO_2$ level in the patient's exhaled air. This indicates the location of the endotrachael tube properly in the patient's pulmonary system.

The top housing 16 and 16a and bottom housing 18 and internal baffles 56 and 62 are made from a polymer such as polycarbonate, styrene, or other like polymer. The spring 42 is made from steel phosphor bronze or molded plastic and the membrane 44 is an elastomer. The cap or disc 26 and 26a is a clear plastic such as a polycarbonate, styrene or other like polymer.

Other equivalent components can be substituted for the components employed in the monitor 10 or 10a to have substantially the same function, in substantially the same way and create substantially the same result.

What is claimed for Letters Patent is:

1. A self-contained diagnostic monitor for determining both air pressure and carbon dioxide ($CO_2$) content in a patient monitoring system, the monitor comprising:
   a housing having a first and second port leading inside the housing, a $CO_2$ detector containing a calorimetric $CO_2$ detection material mounted within the housing and a manometer for indicating pressure to and from the patient mounted within the housing, the housing having a clear cover portion for viewing the $CO_2$ detection material and a pressure indicator on the manometer.

2. The diagnostic monitor according to claim 1 wherein the housing has a first and second housing component attached together to retain the $CO_2$ detector and manometer inside the housing.

3. The diagnostic monitor according to claim 2 wherein the first housing component is a top housing having the first port adapted to be connected to a ventilation system and the second housing component is a bottom housing having the second port adapted to be connected to a patient ventilation tube.

4. The diagnostic monitor according to claim 3 wherein the $CO_2$ detection material is mounted within the top housing on a support frame.

5. The diagnostic monitor according to claim 4 wherein the support frame has a central annular bore and openings for passage of air, a shaft with an outer helical configuration and a pointer at a top portion rotating with the shaft, the shaft passing through the central annular bore and a central hole in the $CO_2$ detection material supported on the support frame.

6. The diagnostic monitor according to claim 4 wherein a top surface of the $CO_2$ detection material is adhesively attached to a bottom surface of the clear cover and the clear cover has downwardly projecting legs engaged to an annular support frame.

7. The diagnostic monitor according to claim 3 wherein the bottom housing second port is axially aligned with the first port.

8. The diagnostic monitor according to claim 3 wherein the bottom housing has a receptacle at a portion distal from the second port, the receptacle containing a spring overlaid by a membrane, the membrane connected to a hollow stem directed upwardly from a central portion of the membrane, the hollow stem having a notch on an inside wall.

9. The diagnostic monitor according to claim 8 wherein the notch on an inside wall of the hollow stem receives a helical configuration from a shaft, a top portion of the shaft having a pointer, the pointer turning towards indicia along an outer edge of the clear cover when the membrane receives air to and from the patient.

10. The diagnostic monitor according to claim 9 wherein the bottom housing contains a first and second baffle and a filter therebetween, a central hole in the first and second baffle and filter permitting passage of the hollow stem.

11. The diagnostic monitor according to claim 1 wherein a surface of the $CO_2$ detection material exposed to exhaled air is covered with backing paper prior to operation of the monitor, the backing paper adapted to be removed prior to a first exposure to the exhaled air.

12. A self-contained diagnostic monitor for determining both air pressure and carbon dioxide content in a patient monitoring system, the monitor comprising:
   top housing sealed to a bottom housing, the top housing having a first port adapted to be connfected to a ventilation system at a first end portion, a support frame supporting a $CO_2$ detector consisting of colorimetric impregnated paper, the support frame having a central annular bore and openings for passage of air, a shaft having an outer helical configuration and a pointer at a top portion rotating on the shaft, the pointer responsive to pressure flow variations, the shaft passing through the impregnated paper and the central annular bore and a visually clear cap sealed to the top housing over the shaft and support frame;
   the bottom housing having a second port adapted to be connected to a patient ventilation tube, the first and second port axially aligned when the top housing is joined to the bottom housing;
   the bottom housing having a receptacle at a portion distal from the second port, the receptacle containing a spring overlaid by a membrane, the membrane connected to a hollow stem directed upwardly from a central portion of the membrane, the hollow stem having a notch on an inside wall for receipt of the helical configuration from the solid shaft, a first baffle overlaying the membrane, a filter overlaying the first baffle and a second baffle overlaying the filter, the first and second baffles and filter having bores for passage of the hollow stem, so that when the top and bottom housings are joined together, air from a ventilation system or patient flows through the monitor and air pressure flow and $CO_2$ presence over $CO_2$, in ambient air are determined by visual inspection through the clear cap.

13. The diagnostic monitor according to claim 12 wherein the clear cap has an outer peripheral portion containing indicia to which the pointer is directed when the membrane receives exhaled air from the patient.

14. A self-contained diagnostic monitor for determining both air pressure and carbon dioxide content in a patient monitoring system, the monitor comprising:
   a top housing having a first port adapted to be connected to a ventilation system and an adjacent support frame having an annular opening with multiple inwardly projecting flanges, a clear disc having downwardly descending legs engaged between the flanges, a top surface of a calorimetric $CO_2$ detector paper adhesively attached to a bottom surface of the clear disc, a shaft having an outer helical configuration and a pointer at a top portion rotating with the shaft, the pointer responsive to pressure flow variations, the shaft rotating under the $CO_2$ detector paper and the pointer projecting from under the $CO_2$ detector paper and pointing towards indicia on an outer annular portion of the clear disc;

a bottom housing having a second port adapted to be connected to a patient ventilation tube and the bottom housing attached to the top housing;

the bottom housing having a receptacle at a portion distal from the second port, the receptacle containing a spring overlaid by a membrane, the membrane having a hollow stem directed upwardly from a central portion of the membrane, the hollow stem having a notch on an inside wall for receipt of the helical configuration on an outside surface of the shaft, a first baffle overlaying the membrane, a filter overlaying the first baffle and a second baffle overlaying the filter, the first and second baffles and filter having bores for passage of the hollow stem, so that when the top and bottom housings are joined together, air from a ventilation system or patient flows through the monitor and air pressure and $CO_2$ presence over $CO_2$ in ambient air are determined by visual inspection through the clear disc.

15. The diagnostic monitor according to claim 14 wherein the clear disc is a polymer.

16. The diagnostic monitor according to claim 14 wherein the first and second port are axially aligned when the top and bottom housing are joined together.

17. The diagnostic monitor according to claim 14 wherein the calorimetric $CO_2$ detector paper has a backing paper adhesively attached to a bottom surface of the detector paper, the backing paper adapted to be removed through a slot in a side surface of the clear disc.

18. The diagnostic monitor according to claim 17 and wherein a sealing ring is positioned between the clear disc the support frame so that when the backing paper is removed, the slot in the side surface of the clear disc is covered.

* * * * *